US008355559B2

(12) United States Patent
Harada et al.

(10) Patent No.: US 8,355,559 B2
(45) Date of Patent: Jan. 15, 2013

(54) METHOD AND APPARATUS FOR REVIEWING DEFECTS

(75) Inventors: Minoru Harada, Fujisawa (JP); Ryo Nakagaki, Kawasaki (JP); Kenji Obara, Kawasaki (JP); Atsushi Miyamoto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 786 days.

(21) Appl. No.: 12/428,557

(22) Filed: Apr. 23, 2009

(65) Prior Publication Data

US 2009/0268959 A1 Oct. 29, 2009

(30) Foreign Application Priority Data

Apr. 23, 2008 (JP) ................................ 2008-112515
Apr. 15, 2009 (JP) ................................ 2009-098812

(51) Int. Cl.
*G06K 9/00* (2006.01)
(52) U.S. Cl. ....................................... 382/141; 382/181
(58) Field of Classification Search .................. None
See application file for complete search history.

(56) References Cited

U.S. PATENT DOCUMENTS 7,173,693 B2 * 2/2007 Shibata et al. ............. 356/237.1
7,764,826 B2 * 7/2010 Miyamoto et al. ............ 382/149

FOREIGN PATENT DOCUMENTS

| JP | 2000-067243 | 3/2000 |
| JP | 2001-189358 | 7/2001 |
| JP | 2001-331784 | 11/2001 |
| JP | 2007-003212 | 1/2007 |
| JP | 2007-040910 | 2/2007 |

* cited by examiner

*Primary Examiner* — Gregory J Toatley
*Assistant Examiner* — Juan D Valentin, II
(74) *Attorney, Agent, or Firm* — Antonelli, Terry, Stout & Kraus, LLP.

(57) ABSTRACT

Disclosed is a method for reviewing defects in a large number of samples within a short period of time through the use of a defect review apparatus. To collect defect images steadily and at high throughput, a defect detection method is selected before imaging and set up for each of review target defects in the samples in accordance with the external characteristics of the samples that are calculated from the design information about the samples. The defect images are collected after an imaging sequence is set up for the defect images and reference images in such a manner as to reduce the time required for stage movement in accordance with the defect coordinates of the samples and the selected defect detection method.

16 Claims, 14 Drawing Sheets

FIG.11

| OPERATION SEQUENCE | PROCESSING ID | DEFECT ID | IMAGE TYPE | COORDI-NATES | MAGNIFI-CATION | DEFECT DETECTION METHOD | REFERENCE IMAGE INDEX |
|---|---|---|---|---|---|---|---|
| 1 | (a) | E | REFERENCE | (x1,y1) | 15000 | — | 1 |
| 2 | (a) | D | REFERENCE | (x2,y2) | 15000 | — | 2 |
| 3 | (a) | E | DEFECT | (x3,y3) | 15000 | — | 1 |
| 4 | (b) | E | — | — | — | DIE COMPARISON | 1 |
| 5 | (c) | E | — | — | — | — | 1 |
| 6 | (a) | E | DEFECT | (x4,y4) | 50000 | — | — |
| 7 | (a) | A | REFERENCE | (x5,y5) | 15000 | — | 3 |
| 18 | (b) | C | — | — | — | HISTORY IMAGE COMPARISON | 1 |
| 19 | (c) | C | — | — | — | — | — |
| 20 | (a) | C | DEFECT | (x13,y13) | 50000 | — | — |

METHOD AND APPARATUS FOR REVIEWING DEFECTS

CLAIM OF PRIORITY

The present application claims priority from Japanese Patent Application JP 2008-112515 filed on Apr. 23, 2008 and Japanese Patent Application JP 2009-98812 filed on Apr. 15, 2009, the content of which is hereby incorporated by reference into this application.

BACKGROUND OF THE INVENTION

The present invention relates to a defect review apparatus, such as a review SEM, which is used to review and analyze the details of a sample's defect that is detected as defect coordinates by a defect inspection apparatus. The present invention also relates to a method for reviewing and analyzing the details of a defect with a review SEM or other defect review apparatus.

For improvement of yield in semiconductor manufacturing, it is important that the cause of defect generation during a manufacturing process be immediately investigated. At semiconductor manufacturing sites, defects are currently analyzed with a defect inspection apparatus and a defect review apparatus. The defect inspection apparatus reviews wafers with optical means or electron beams and outputs detected defect coordinates. It is important that the defect inspection apparatus rapidly process a broad area. Therefore, the defect inspection apparatus reduces the amount of image data by maximizing the pixel size (that is, by lowering the resolution) of an image to be acquired. In most cases, a detected low-resolution image may indicate the presence of any existing defect, but does not precisely identify its type. Under such circumstances, the defect review apparatus is used to precisely identify the type of a defect detected by the defect inspection apparatus. The defect review apparatus uses an output generated by the defect inspection apparatus, picks up a high-resolution image of a wafer at defect coordinates, and outputs the picked-up image. As the defect size is now on the order of several tens of nanometers due to an increased degree of miniaturization, the semiconductor manufacturing process requires a resolution on the order of several nanometers in order to review the details of defects. As such being the case, a defect review apparatus based on a scanning electron microscope (hereinafter referred to as the review SEM) has been widely used in recent years. An automated defect review operation is called for in a semiconductor mass production line. As described in JP-A-2001-331784, the review SEM incorporates an ADR (automatic defect review) function, which automatically acquires an image at defect coordinates of a sample, and an ADC (automatic defect classification) function, which automatically classifies acquired images.

Conventional technologies incorporated into a defect review apparatus composed of a review SEM are also described in JP-A-2001-189358, JP-A-2000-67243, JP-A-2007-40910, and JP-A-2007-3212.

The technology described in JP-A-2001-189358 is such that the inspection result information cut out from a defect inspection apparatus includes the information about a comparison target in addition to the information about a defect. The microscope system (review SEM system) described in JP-A-2001-189358 detects a defect image and a comparison target image in accordance with the comparison target information and compares the images to locate the defect.

The technology described in JP-A-2000-67243 is such that an electron microscope is used to automatically detect singularities (e.g., refraining from moving to a reference point when no pattern or repetitive patterns are encountered) in accordance with defect/foreign matter coordinates and other inspection result information cut out from a defect inspection apparatus, and review or process the information about the detected singularities.

A defect review apparatus described in JP-A-2007-40910 uses a scanning electron microscope to acquire a low-magnification image showing a defect in a sample, which is detected by an inspection apparatus, synthesizes a reference image by making use of the recurrence period of a circuit pattern that is imaged on the basis of the acquired low-magnification defect image showing the defect, detects the defect by comparing the synthesized reference image and the acquired low-magnification defect image showing the defect, and picks up a high-magnification image of the detected defect.

An imaging recipe creation apparatus described in JP-A-2007-3212 creates an imaging recipe for reviewing a semiconductor pattern with a scanning electron microscope. This image recipe creation apparatus includes a database and an imaging recipe creator. The database receives the layout information about a semiconductor pattern (an image picked up with a scanning electron microscope, CAD data containing the design information about the semiconductor pattern, or a CAD image obtained by converting the CAD data containing the design information about the semiconductor pattern into image data) in a low-magnification visual field and stores the input information. The imaging recipe creator automatically creates the imaging recipe by following an automatic creation algorithm containing a selection rule for selecting an imaging point optimized by means of teaching based on the semiconductor pattern layout information stored in the database.

In recent years, the number of defects to be reviewed per wafer has increased due to an increase in the diameters of semiconductor wafers. In addition, the defect review apparatus, such as a review SEM, exhibits a lower throughput than the defect inspection apparatus. Consequently, the speed of ADR needs to be increased.

In ADR, a considerable amount of time is generally spent on moving a stage between an initial position and a target position and on picking up a reference image and a defect image. Therefore, the speed of ADR can be effectively increased by shortening the time required for stage movement and eliminating some imaging procedures. However, such an increase in the speed of ADR is not sufficiently studied in any of the above-mentioned patent documents.

To consistently detect defects in a sample (semiconductor wafer) at a high throughput with a review SEM or other defect review apparatus, a user of the apparatus has to properly select and set up various defect detection methods in accordance with various characteristics of the sample to be placed on the apparatus. However, the proper selection and setup of various defect detection methods according to the various characteristics of the sample are not sufficiently studied in any of the above-mentioned patent documents.

SUMMARY OF THE INVENTION

The present invention relates to a defect review method and defect review apparatus that make it possible to consistently review the details of a defect at a high throughput by using the design information about a circuit pattern formed on a semiconductor wafer or other sample placed on the apparatus when a review SEM or other defect review apparatus is used to review the details of a defect in the sample, which is detected by a defect inspection apparatus.

The present invention provides a defect review method and defect review apparatus that are applicable to a situation where a review SEM or other defect review apparatus is used to review a target defect in a sample, which is detected as defect coordinates by a defect inspection apparatus. The features of the defect review method and defect review apparatus according to the present invention are summarized below:

(1) As regards each review target defect in a sample, the sample's external characteristics in a defect region are calculated from design information. In accordance with the obtained external characteristics, a defect detection method is selected and set up before an SEM image of the defect region is picked up. The defect region is a large, low-magnification SEM imaging region that is centered around the coordinates of a defect detected by a defect inspection apparatus and set up in accordance with the amount of position error in the defect inspection apparatus or the like. The sample's external characteristics based on the design information indicate whether repetitive patterns exist over the entire surface of the defect region in an evenly-spaced manner. If evenly-spaced repetitive patterns exist, a reference-less method is selected as the defect detection method. If a matching pattern is retrieved from history data in a situation where no evenly-spaced repetitive patterns exist, a history comparison method is selected. If a matching pattern is retrieved from the vicinity, a vicinity comparison method is selected. In the other situation, a die comparison method is selected.

(2) When a defect detection method is set up for all review target defects before reviewing the sample, the imaging sequence for a defect image and a reference image (as needed) is set up so as to shorten the stage movement time in accordance with the sample's defect coordinates and the selected defect detection method. A processing recipe is then set up in accordance with the imaging sequence. The processing recipe includes an execution sequence, which is a combination of (a) an imaging process, (b) a defect detection process based on a defect detection method, and (c) a defect detection method setup process, and parameters for each process. At the time of reviewing, (a) the imaging process, (b) the defect detection process based on a defect detection method, and (c) the defect detection method setup process are executed in accordance with the processing recipe to collect defect images.

(3) To reduce the time required for reference image pickup, the design information is used to retrieve a reference image pickup region from a region where image pickup can be achieved without moving the stage from a defect image pickup position. When the region to be retrieved is found, it is handled as a reference image pickup region.

(4) To minimize the time required for reference image pickup, the design information is used to retrieve an image available as a reference image from a history database, which stores previously picked-up images. When the image to be retrieved is found, it is used as a reference image.

According to one aspect of the present invention, there are provided a method and apparatus (e.g., review SEM) for reviewing a target defect in a sample that is detected as the coordinates of a defect by a defect inspection apparatus. The defect review method includes a search step of cutting out the design information about a peripheral region around the coordinates of the defect and the design information about a defect region substantially centered around the coordinates of the defect from the design information about the sample, and searching, in accordance with the cut-out design information about the peripheral region and about the defect region, the peripheral region for a reference region that is designed to have the same appearance as the defect region; an image acquisition step of picking up a defect image of the defect region and picking up a reference image of the reference region retrieved in the search step; and a review step of comparing the defect image acquired in the image acquisition step against the reference image to detect and review the review target defect.

According to another aspect of the present invention, there are provided a method and apparatus for reviewing a target defect in a sample that is detected as the coordinates of a defect by a defect inspection apparatus. The method includes a search step of cutting out the design information about a defect region substantially centered around the coordinates of a defect from the design information about the sample, and searching the reference images of a plurality of reference regions stored as history data for the reference image of a reference region designed to have the same appearance as the defect region by comparing the cut-out design information about the defect region against the design information about the plurality of reference regions stored as the history data; an image acquisition step of picking up a defect image of the defect region and picking up a reference image of the reference region retrieved in the search step; and a review step of comparing the defect image acquired in the image acquisition step against the reference image to detect and review the target defect.

According to still another aspect of the present invention, there are provided a method and apparatus for reviewing review target defects in a sample that are detected as the coordinates of a defect by a defect inspection apparatus. The method includes a setup step of cutting out the design information about a defect region substantially centered around the coordinates of a defect from the design information about the sample, and selecting a defect detection method for each of the review target defects in accordance with the cut-out design information about the defect region; an image acquisition step of acquiring a defect image by imaging at least the defect region of each of the review target defects; and a review step of detecting and reviewing each of the review target defects in accordance with the defect image acquired in the image acquisition step by using the defect detection method selected in the setup step.

The present invention enables a review SEM or other defect review apparatus to use the design information about a sample and automatically set up a defect detection method appropriate for the external characteristics of a circuit pattern in a defect region without picking up an image of the sample. This makes it possible to automatically collect defect images at a high throughput and with high consistency.

These and other objects, features, and advantages of the present invention will be apparent from the following more particular description of preferred embodiments of the present invention, as illustrated in the accompanying drawings.

BRIEF DESCRIPTION OF THE DRAWINGS

FIG. 11 illustrates an embodiment of processing recipe setup.

DETAILED DESCRIPTION OF THE PREFERRED EMBODIMENTS

Embodiments of the present invention of a method and apparatus for reviewing defects will now be described with reference to the accompanying drawings.

First Embodiment

A semiconductor substrate review SEM (Scanning Electron Microscope) that is a first embodiment of the present invention of a method and apparatus for reviewing defects will now be described. A defect review apparatus based on the review SEM according to the present invention incorporates an ADR (Automatic Defect Review) function for automatically collecting images at defect coordinates of a sample and an ADC (Automatic Defect Classification) function for automatically classifying obtained images.

Figure 1:
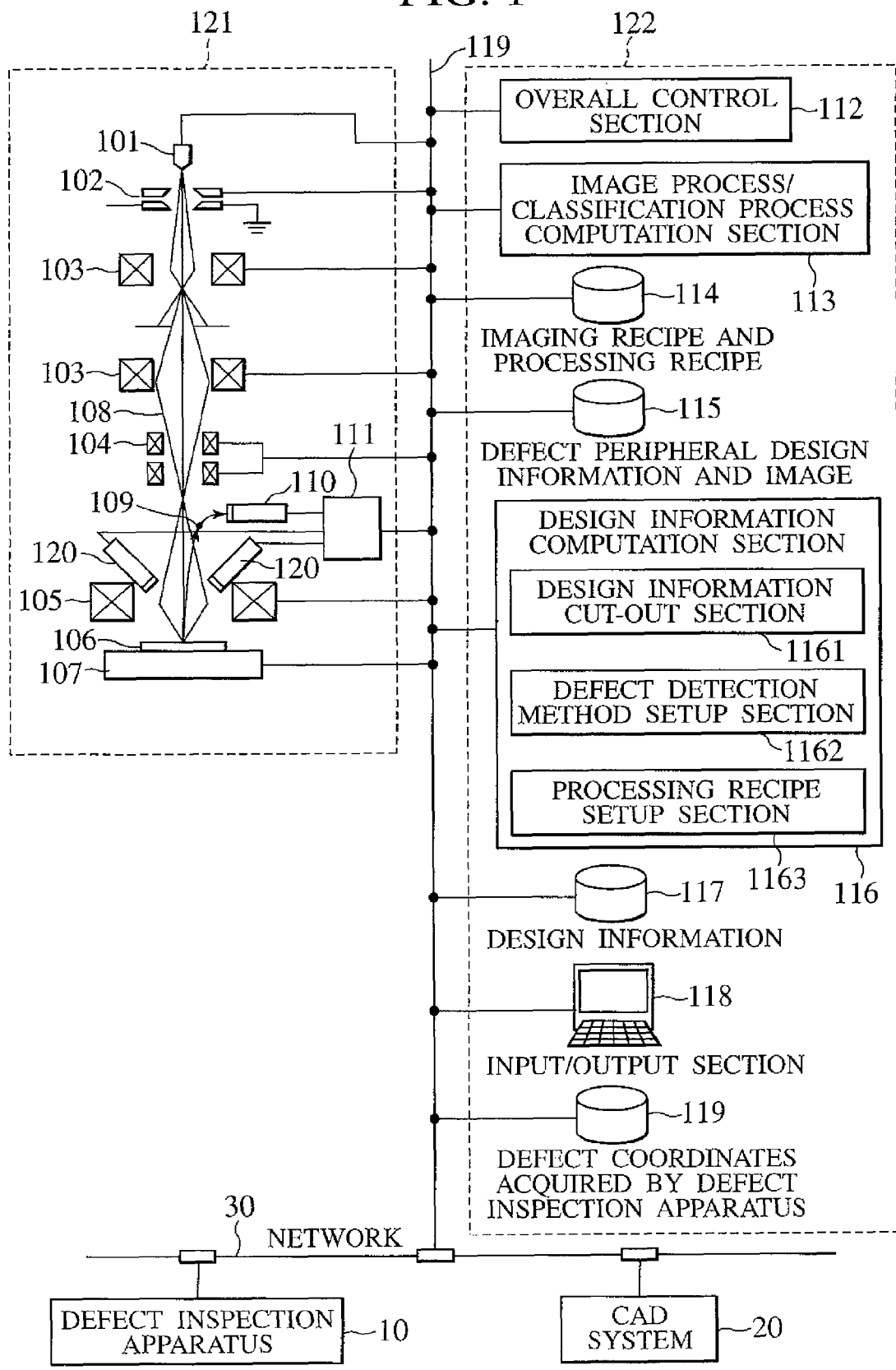
FIG. 1 is a diagram illustrating an embodiment of a review-SEM-based defect review apparatus.

FIG. 1 shows the configuration of the review SEM according to the present invention. The review SEM according to the present invention includes an SEM image acquisition section 121 and a signal processing section 122. A bus 119 is connected between the SEM image acquisition section 121 and the signal processing section 122. The SEM image acquisition section 121 includes an electron source 101 for generating primary electrons 108, an acceleration electrode 102 for accelerating the primary electrons, a focusing lens 103 for converging the primary electrons, a deflector 104 for scanning and deflecting the primary electrons two-dimensionally, and an objective lens 105 for converging the primary electrons on a sample 106. The reference numeral 107 denotes a stage that carries the sample 106 and can move in X and Y planes. The SEM image acquisition section 121 also includes a detector 110 for detecting secondary electrons 109 generated from the sample, a detector 120 for detecting primary electrons reflected from the surface of the sample, and a digitization section 111 for digitizing signals detected by the detectors 110, 120 by subjecting them to analog-to-digital conversion. All the above-mentioned component elements are connected to an overall control section 112 via the bus 119.

The signal processing section 122 includes the overall control section 112; an image processing/classification computation section 113, which performs image processing or classification on an SEM image acquired by the SEM image acquisition section 121; a storage section 114, which stores review condition information (imaging recipe) that is input from an input/output section 118, and stores a processing recipe (a defect review sequence included) that is set up by a processing recipe setup section 1163 of a design information computation section 116; a storage section 115, which stores image data that is picked up by the SEM image acquisition section 121 as history data, and stores the design information about a defect region (defect peripheral region) that is cut out by a design information cut-out section 1161; the design information computation section 116, which includes the design information cut-out section 1161, a defect detection method setup section 1162, and the processing recipe setup section 1163, and performs computations on the design information about a semiconductor substrate (sample); a storage section 117, which stores the design information about a semiconductor substrate (sample) that is input from a CAD system 20 via a network 30 or the like; the input/output section 118, which includes, for instance, a keyboard, mouse, and other similar device for giving instructions to the apparatus and a monitor, printer, and other device for outputting data from the apparatus; and a storage section 119, which stores defect coordinates associated with the ID of a defect of a semiconductor substrate (sample) that is detected (acquired) when an inspection is performed by a defect inspection apparatus 10. All the above component elements are interconnected via the bus 119. The storage section 114 also stores a processing recipe that is set up by the processing recipe setup section 1163 of the design information computation section 116.

Figure 2:
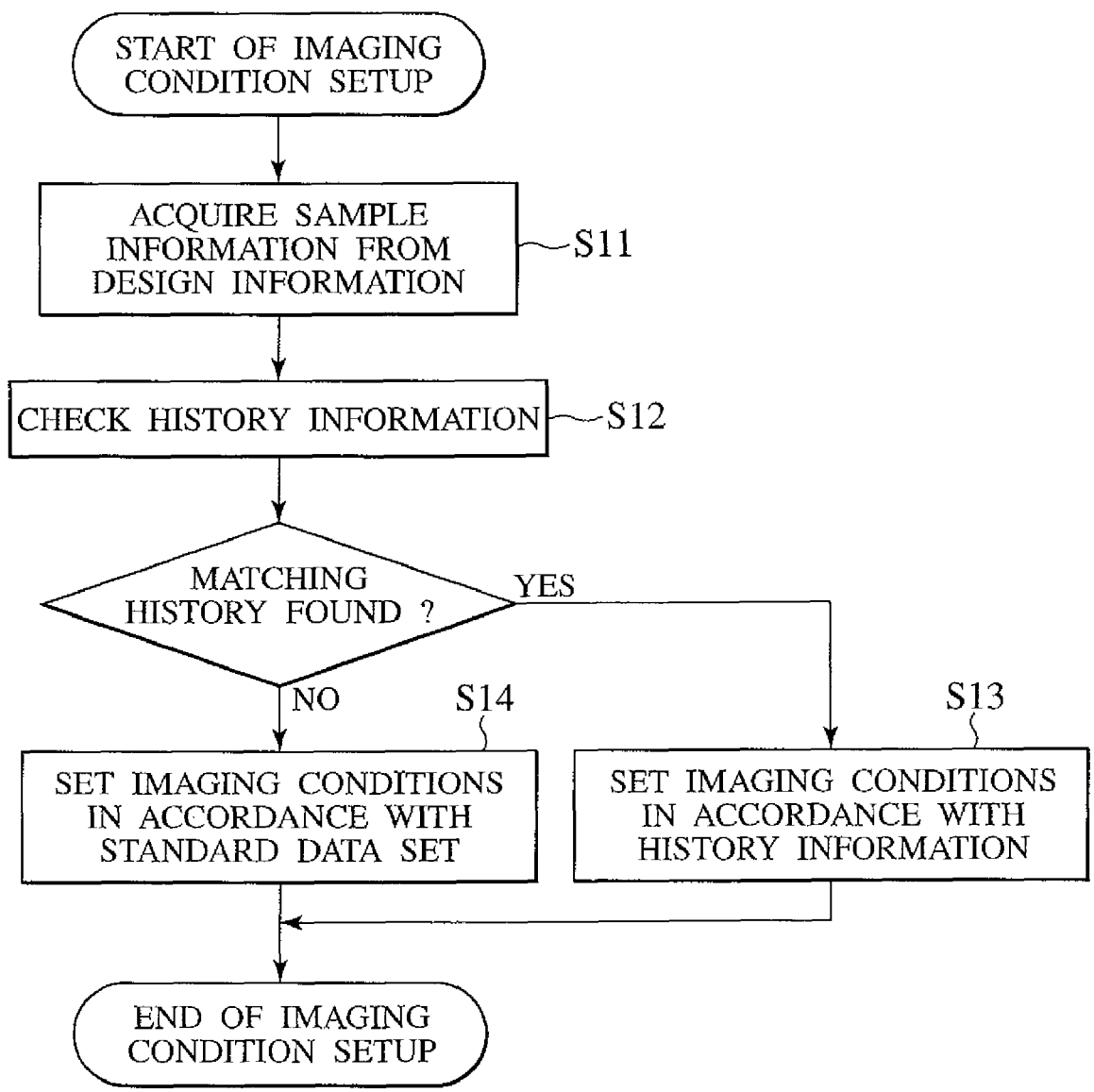
FIG. 2 is a flowchart illustrating an embodiment of an imaging recipe automatic setup process.

FIG. 2 will now be used to describe an automatic setup procedure for electron optical system conditions (SEM imaging conditions), which constitute an imaging recipe for SEM image pickup by the SEM image acquisition section according to the present invention. First of all, the overall control section 112 acquires sample information by searching the design information stored in the storage section 117 in accordance with an input type of a semiconductor substrate (sample) mounted on the stage 107 (step S11). The sample information includes, for instance, the material information about the sample (semiconductor substrate), wiring pattern intervals, and layer information. Next, the overall control section 112 checks whether the storage section 114 has any history data that shows electron optical system conditions (SEM imaging conditions) have been set for semiconductor substrates (samples) that have sample information similar to that acquired (step S12). If found, such history data is used to set the electron optical system conditions (SEM imaging conditions) for the SEM image acquisition section 121 as an imaging recipe (step S13). If, on the other hand, no such history data is found, standard electron optical system conditions (SEM imaging conditions), which are set up beforehand for each sample information and stored in the storage section 114, are set for the SEM image acquisition section 121 as an imaging recipe (step S14). In this manner, the storage section 114 sets the electron optical system conditions (SEM imaging conditions) for SEM image pickup as an imaging recipe for each sample information (each sample type), thereby simplifying SEM imaging condition setup. The electron optical system conditions (SEM imaging conditions) include, for instance, an acceleration voltage, a probe current, and an imaging magnification.

Figure 3:
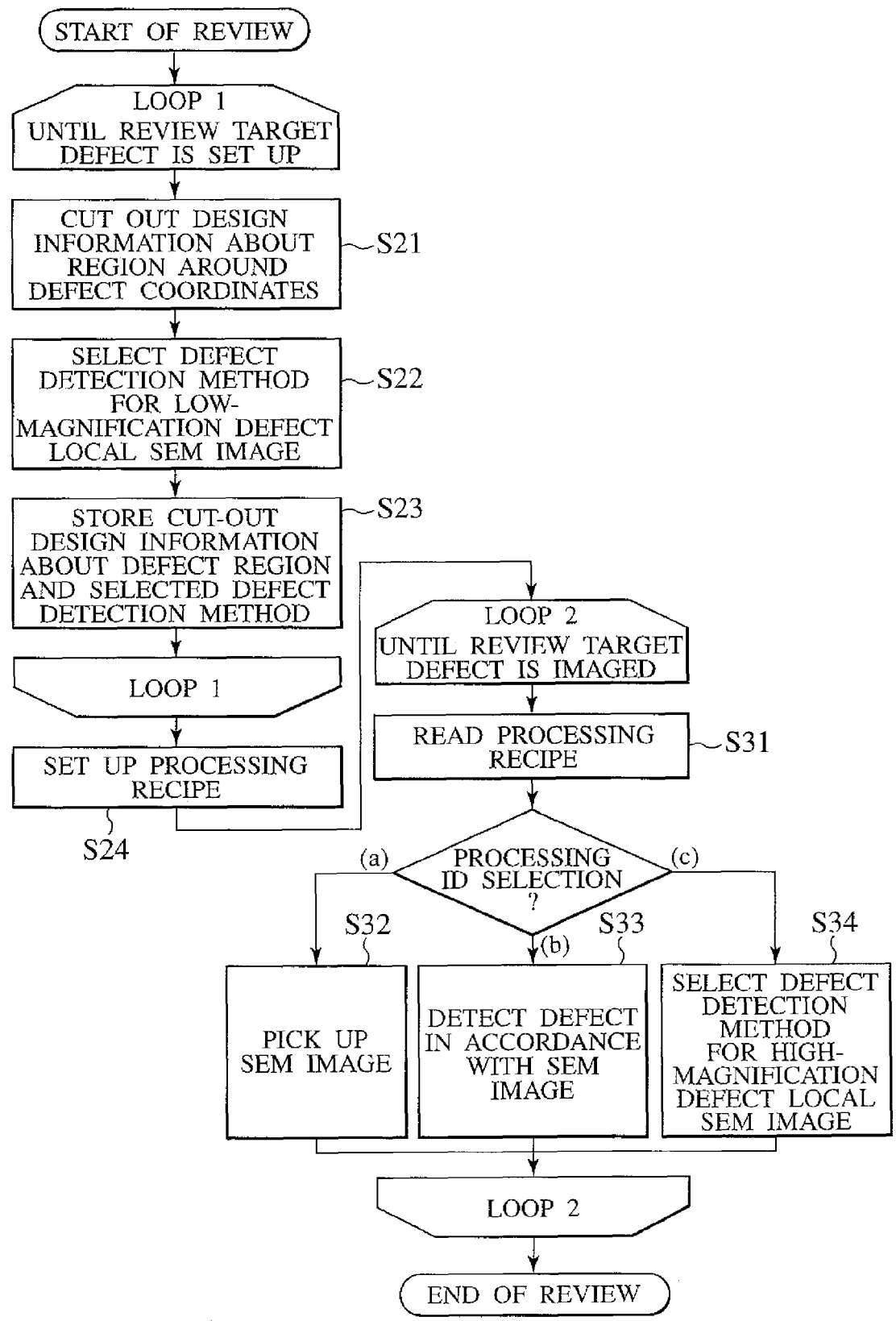
FIG. 3 is a flowchart illustrating a first embodiment of an ADR sequence that is performed by a review-SEM-based defect review apparatus.

An automatic defect review method employed by the review SEM according to the present invention will now be described. First of all, a semiconductor substrate (semiconductor wafer) 106 is mounted on the stage 107 before imaging. The overall control section 112 selects an imaging recipe from a plurality of imaging recipes stored in the storage section 114 in accordance with the type of the semiconductor substrate mounted on the stage 107, which is entered via the input/output section 118, and controls the ADR function, which automatically collects SEM images at review target defect coordinates of the sample, and the ADC function, which automatically classifies the automatically collected SEM images, in accordance with the conditions (processing recipe (a defect review sequence included)) stored in the storage section 114. It is assumed that the stored imaging recipes include various electron optical system conditions for SEM imaging (such as an acceleration voltage, a probe current, and an imaging magnification). Next, the overall control section 112 accesses the storage section 119 and reads the coordinate information about defect IDs of the semiconductor substrate, which are detected beforehand during an inspection conducted by a defect inspection apparatus 10 and will be reviewed by the review SEM. In accordance with the read coordinate information about each of the defect IDs, the design information computation section 116 performs steps S21 to S23, which are included in loop 1 as indicated in FIG. 3, performs step S24 to set up a processing recipe, including a defect detection method, for every review target defect ID, and store the processing recipe in the storage section 114. The overall control section 112 and other relevant component elements automatically collect defect SEM images (exercise the ADR function) by performing loop 2 steps (S31 to S34) for every review target defect ID in accordance with a processing recipe (processing IDs and processing parameters arranged according to an execution sequence (operation sequence)) shown, for instance, in FIG. 11, which is stored in the storage section 114.

To pick up an image of defect in a sample at a high magnification, it is necessary to perform the following image pickup steps. First of all, the stage 107 is moved so that the coordinates of a defect are positioned within an imaging range of an electron optical system of the SEM image acquisition section 121. In general, there is an error of approximately ±4 µm between the coordinates of an actual defect and the coordinates of a defect that is detected beforehand during an inspection conducted by a defect inspection apparatus 10 and read from the storage section 114. To position a defect within a visual field, therefore, the SEM image acquisition section 121 picks up an image in a visual field of approximately 9 µm and at a low-magnification (at a magnification between 5,000× and 20,000×, that is, at a magnification, for instance, of 15,000×). However, if an image is picked up at a low magnification, the details of a defect cannot be reviewed. Therefore, the image processing/classification computation section 113 (which functions as a defect detection section and a review process section) of the signal processing section 122, for example, detects defect coordinates from an SEM image picked up at a low magnification. The SEM image acquisition section (image acquisition section) 121 uses the detected defect coordinates to pick up an image at a high magnification (at a magnification between 20,000× and 100,000×, that is, at a magnification, for instance, of 50,000×), and stores the image, for instance, in the storage section 115.

FIG. 3 will now be used to describe a sequence that the defect review apparatus (review SEM) according to the present invention performs to automatically collect defect images of a sample. This sequence is performed by setting up a processing recipe in accordance with the defect coordinates of a sample, which are detected by a defect inspection apparatus, and the design information about the sample, and detecting and imaging defects in accordance with the processing recipe.

A first feature of the present invention is such that the design information computation section 116 of the signal processing section 122 sets up a defect detection method for each review target defect without picking up its SEM image by performing loop 1 steps (S21 to S23) in accordance with the design information about a defect region, which is cut out from the design information about a sample in accordance with defect coordinates of the sample that are detected by a defect inspection apparatus 10, and sets up a processing recipe in step S24, that is, before it is processed within loop 2, in accordance with the defect coordinates of the sample, which are detected by the defect inspection apparatus 10, and with the defect detection method that was set as mentioned above.

Figure 4:
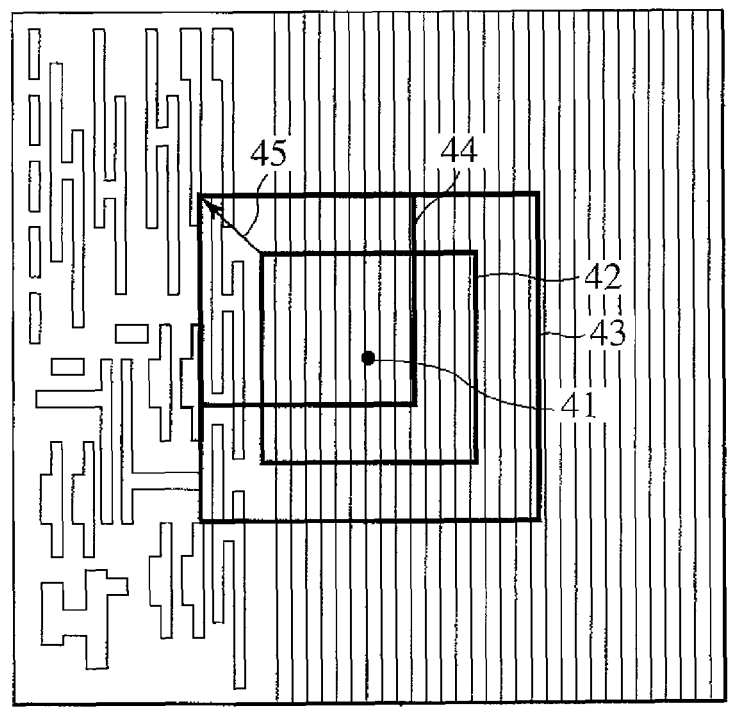
FIG. 4 is a diagram illustrating an embodiment of a method of setting up a region from which design information is to be cut out.
Figure 5:
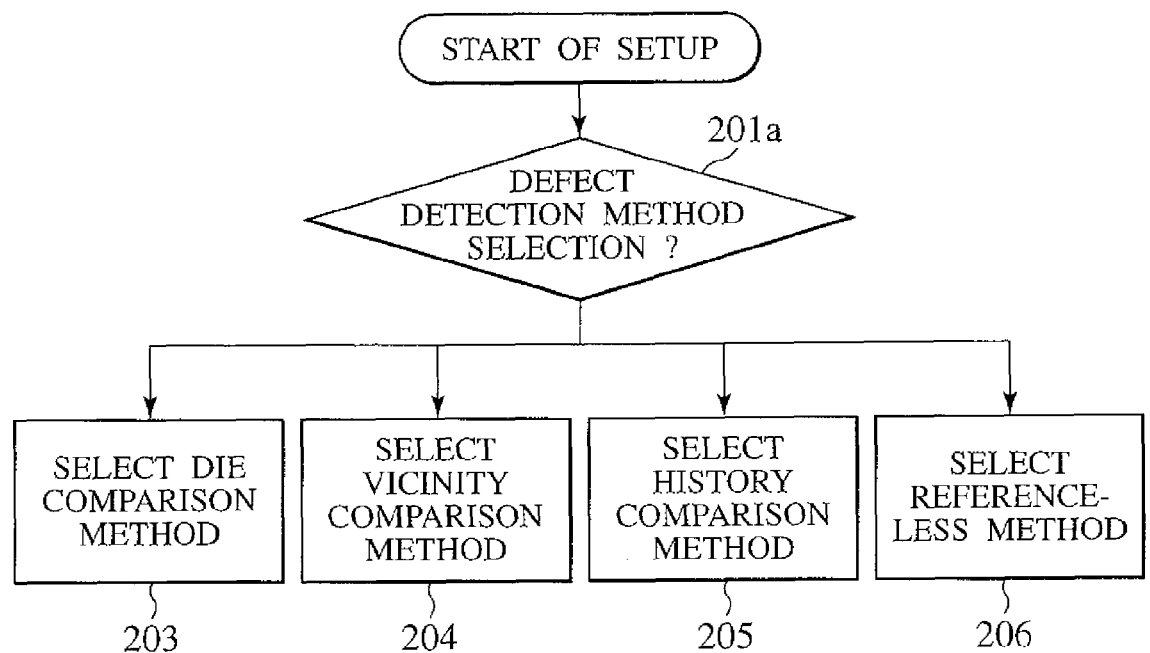
FIG. 5 is a schematic diagram illustrating an embodiment of defect detection method selection for a low-magnification defect local SEM image.
Figure 6:
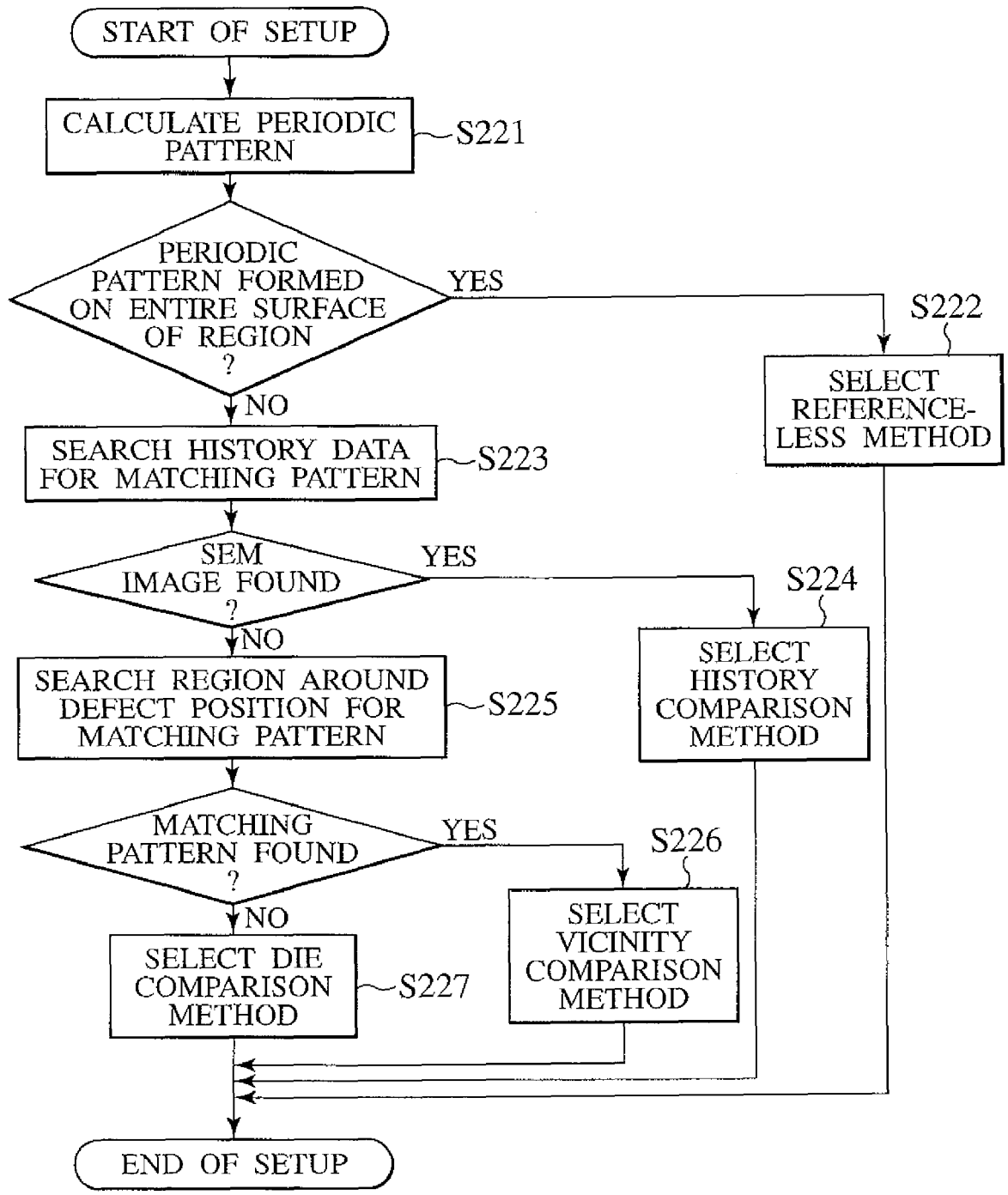
FIG. 6 is a flowchart illustrating the first embodiment of a defect detection method setup process for a low-magnification defect local SEM image.

First of all, the loop 1 steps (S21 to S23) will be described. As indicated in FIG. 4, the design information cut-out section 1161 of the design information computation section 116 cuts out the design information about a defect region 43 from the design information about a semiconductor substrate (sample), which is stored in the storage section 117, in accordance with the defect coordinates 41 of a defect ID of the sample that is detected by the defect inspection apparatus 10 and stored in the storage section 119 (step S21). "Cutting out the design information about the semiconductor substrate (sample)" as used herein means paying attention to the design information about a particular region of the entire surface of the sample. A method of setting up the defect region 43, which is the region from the design information is to be cut out, will be described later with reference to FIG. 4. As shown in FIGS. 5 and 6, the defect detection method setup section 1162 then sets up various defect detection methods (die comparison method, vicinity comparison method, history comparison method, reference-less method, etc.) for low-magnification defect local SEM images in accordance, for instance, with the design information about the defect region, which is cut out by the design information cut-out section 1161. The design information about a defect region, which is cut out in step S21, is correlated with a defect ID and stored in the storage section 115, whereas each of the defect detection methods, which is set up in step S22, is correlated with a defect ID and stored in the storage section 114 as a part of a processing recipe (step S23). As described above, the defect detection methods for all the defects to be reviewed are set up when the loop 1 steps (S21 to S23) are completed.

Next, the first embodiment in which the defect detection method setup section 1162 according to the present invention selects a defect detection method and stores it in the storage section 114 as a defect detection method for a processing recipe in accordance with the design information about a defect region that is cut out by the design information cut-out section 1161 and stored in the storage section 115 will be described with reference to FIGS. 4 to 9.

As the defect coordinates 41 of a sample, which are detected by the defect inspection apparatus 10, contain many positional error components, the defect region 43 from which the design information is to be cut out is set to be larger, for instance, than an imaging region 42 for low-magnification image pickup as shown in FIG. 4 by controlling the deflector 104 so that the SEM does not select a wrong defect detection method. Since the defect coordinates 41 of a sample, which are detected by the defect inspection apparatus 10, contain many positional error components, the defect region 44 is used as a defect region from which the design information is to be cut out for the imaging region 42, which is to be actually imaged by the SEM. As a result, the defect detection method selected in accordance with the design information cut out for the defect region 44 is not fit for an actually picked-up SEM image. When, for instance, a defect detection method is selected in accordance with the design information cut out for the defect region 42, the reference-less method is selected because repetitive patterns exist over the entire surface of the region in an evenly-spaced manner. However, if a defect detection method is selected in accordance with the design information cut out for the defect region 44 due to position error, the reference-less method is not an appropriate method because a non-repetitive pattern exists in a part of the region. Therefore, the defect region for which the design information is to be cut out needs to be set up while considering position error on the basis of the defect coordinates 41 of the sample. A simple method would be to use a defect region 43 that is enlarged by the amount of position error 45, which is estimated beforehand on the basis of the defect coordinates of the sample.

As shown in FIG. 5, when the design information computation section 116 selects a defect detection method (201a) in step S22, various defect detection methods may be selected for a low-magnification defect local SEM image, which is selected and set up in accordance with the history data and the design information about a defect region containing defect coordinates of a sample that are detected by a defect inspection apparatus 10. The available defect detection methods include, for instance, the die comparison method (203), vicinity comparison method (204), history comparison method (205), and reference-less method (206). The die comparison method (203) detects a defect by comparing identical local SEM images of dies because no identical SEM images exist within a die. The vicinity comparison method (204) detects a defect by comparing a defect local SEM image against a neighboring identical reference local SEM image because an identical local SEM image exists in the vicinity. The history comparison method (205) detects a defect by comparing a defect local SEM image against an identical reference local SEM image included in the history data because the history data stored in the storage section 115 includes the identical local SEM image that is already picked up and existing. The reference-less method (206), which is described in JP-A-2007-40910, detects a defect by comparing a defect local SEM image of a region including evenly-spaced repetitive patterns against a reference local SEM image, which is synthesized so as to delete a defect from the defect local SEM image.

An embodiment of a method that the defect detection method setup section 1162 uses to select and set up a defect detection method will now be described with reference to FIG. 6. First of all, the defect detection method setup section 1162 uses the design information (design data) about a defect region 1603, which is cut out and stored in the storage section 115, to perform calculations to judge whether repetitive patterns exist over the entire surface of the defect region in an evenly-spaced manner (step S221). The presence of evenly-spaced repetitive patterns may be checked for by performing calculations on geometrical information indicating the coordinates and length of a circuit pattern that are included in the design information or by performing calculations on an image equivalent of the geometrical information. If the obtained judgment result indicates that repetitive patterns exist over the entire surface of the defect region in an evenly-spaced manner, the reference-less method (206) is selected and set up for use (step S222) because defect detection can be achieved by the reference-less method (206). If, on the other hand, the obtained judgment result does not indicate that repetitive patterns exist over the entire surface of the defect region in an evenly-spaced manner, step S223 is performed to access the storage section 115, which stores the relationship between the design information about a defect region and the reference local SEM image picked up as the history data, and search for a history reference local SEM image that is similar in appearance to a review target defect region and picked up so as to exclude a defect. The search method to be used will be described later with reference to FIGS. 7, 10A, and 10B. If the history reference local SEM image, which is without a defect and similar in appearance to the review target defect region, is already picked up and existing as the history data, step S224 is performed to select and set up the history comparison method (205) for use because it detects a defect by comparing the defect local SEM image of the defect region against the history reference local SEM image, which is found within the history data a result of the above search. If, on the other hand, the history reference local SEM image is not already picked up and existing as the history data, step S225 is performed by a later-described method to search the vicinity of the defect region for a pattern that is identical with the pattern of the defect region. If such an identical pattern is found in the vicinity, step S226 is performed to select and set up the vicinity comparison method (204) because it detects a defect by comparing the defect local SEM image against a reference local SEM image of the vicinity. If, on the other hand, no such identical pattern is found in the vicinity, step S227 is performed to select and set up the die comparison method (203) because it detects a defect by comparing the defect local SEM image against the reference local SEM image of a reference region that is correlated with the defect coordinates of a neighboring die.

Figure 7:
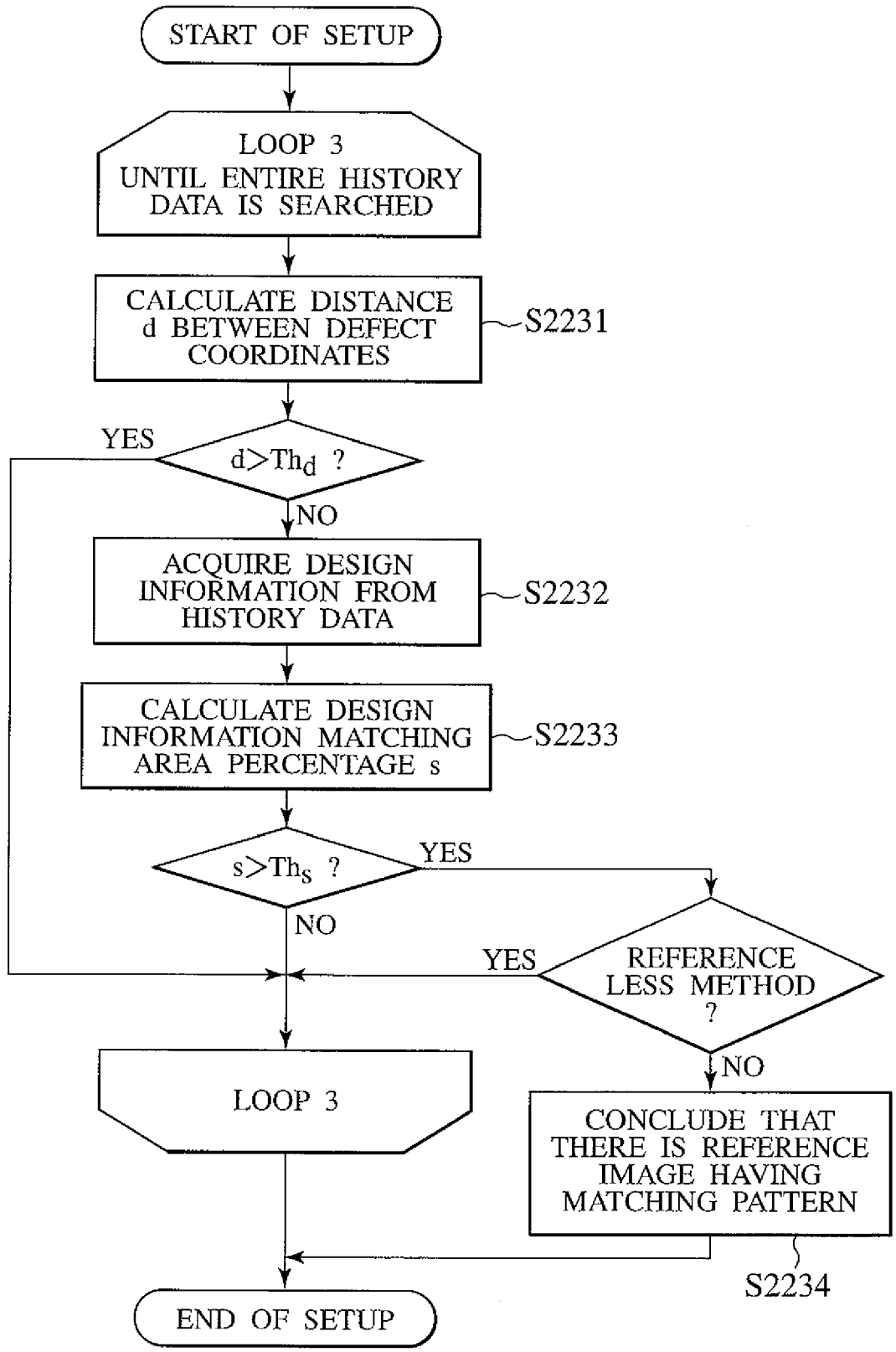
FIG. 7 is a flowchart illustrating an embodiment of a process that is performed to search for a matching pattern in history data stored in a storage section.
Figure 8:
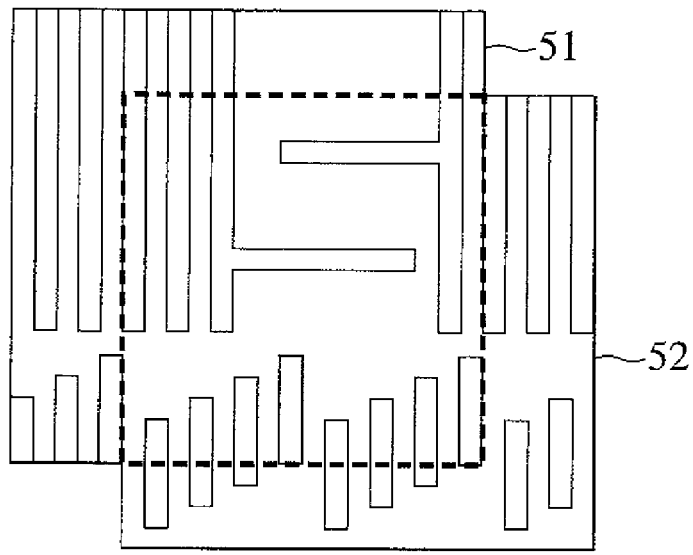
FIG. 8 is a diagram illustrating an embodiment of a matching area percentage of sample design information.

A process performed in step S223 will now be described with reference to FIGS. 7, 10A, and 10B. In step S223, the overall control section 112 and the design information computation section 116 (design information cut-out section 1161 and defect detection method setup section 1162) operate to search the history data stored in the storage section 115 for a history reference local SEM image that is to be used with the history comparison method. Steps S2231 to S2234 within loop 3 are performed to search the whole history data stored in the storage section 115 (e.g., the defect coordinates (die coordinates of defects) and design information concerning defect regions 702 to 706). To prevent the search time from increasing due to an increase in the number of history data, it is assumed that defect regions having the same appearance within a single die are not positioned apart from each other by more than a predetermined distance. First of all, step S2231 is performed to calculate the distance d between the defect coordinates of a review target (e.g., the die coordinates of defect (C) in defect region 704), which are detected by a defect inspection apparatus 10, and the defect coordinates of history data (e.g., the die coordinates of defects (A), (B), (D), and (E) of defect regions 702, 703, 705, and 706). If the distance d is greater than a threshold value $Th_d$ ($d>Th_d$), it is judged that no identical patterns are found in the associated history data (e.g., defect region 706 of defect (E)). If the sample is a semiconductor wafer, a plurality of dies having the same appearance are arranged. Therefore, the coordinates (die coordinates) relative to the origin of each die are used as defect coordinates. The reason is that if the distance between die coordinates within a die is short, it can be expected that identical patterns are designed no matter whether the distance between defect coordinates of a sample is long. If, on the other hand, the distance d is not greater than the threshold value $Th_d$ ($d \leq Th_d$), step S2232 is performed to access the history data stored in the storage section 115 and acquire the design information 51 about defect regions (e.g., defect regions 702, 703, and 705) as shown in FIG. 8. Step S2233 is then performed to calculate the matching area percentage s between the acquired design information 51 about the defect regions (e.g., defect regions 702, 703, and 705) and the design information 52 about a review target defect region (e.g., defect region 704). More specifically, positional alignment is effected between the design information 51 about defect regions (e.g., defect regions 702, 703, and 705), which is derived from the history data, and the design information 52 about a review target defect region (e.g., defect region 704) to calculate the percentage of a matching area s. If the calculated matching area percentage s is greater than a threshold value $Th_s$ ($s>Th_s$) and the defect region is, for instance, defect region 702, which does use the reference-less method as the defect detection method for the history data, step S2234 is performed to judge that a reference local SEM image (e.g., image 707) having the same appearance as the one used with the vicinity comparison method and no defect is already picked up. Thus, the reference local SEM image (e.g., image 707) can be used with the history comparison method (205). As regards defect region 705, for example, it is judged that the matching area percentage s is not greater than the threshold value $Th_s$ ($s \leq Th_s$). As regards defect region 703, for example, the defect detection method for the history data is judged to be the reference-less method because the design information indicates that repetitive patterns exist over the entire surface.

As described above, in step S223, the design information computation section 116 (design information cut-out section 1161 and defect detection method setup section 1162) can access the storage section 115, which stores the history data (e.g., defect coordinates (die coordinates of defects) and design information concerning defect regions 702 to 706), and search for a history reference region (e.g., region 707) designed to have the same appearance as a defect region (e.g., region 704) for the purpose of using a picked-up reference local SEM image (a reference local SEM image picked up at a low magnification as processing ID (a) in operating sequence 7, which is shown in FIG. 11) with the history comparison method (205). In a situation where, for instance, a different layer is formed or a different material is used, a different appearance image is generally picked up even if the design information indicates that identical patterns are formed. Therefore, when a certain set of design information is to be compared against another set of design information, not only the geometrical information but also the layer and material are considered for comparison purposes.

Figure 9:
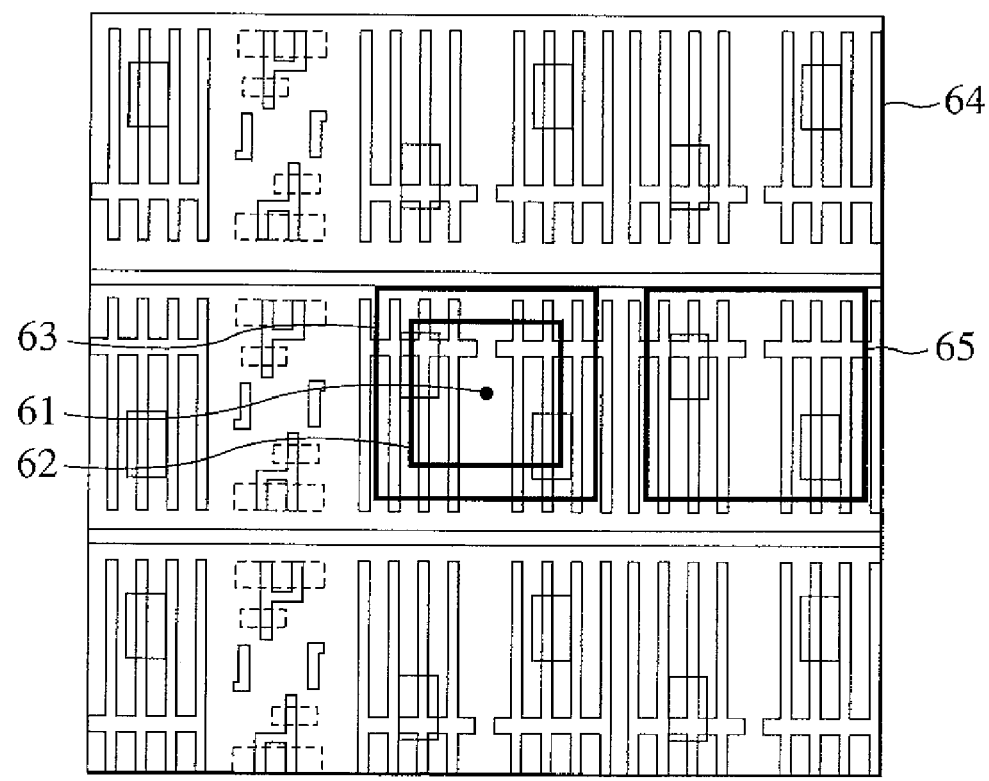
FIG. 9 is a diagram illustrating an embodiment of the result obtained when a peripheral region around a defect is searched for a reference region that is designed to have the same appearance as a defect region.

FIG. 9 will now be used to describe a process (step S225) that the design information computation section 116 performs to search the vicinity of a defect region for a pattern that is identical with a pattern formed in the defect region. Referring to FIG. 9, the reference numeral 61 denotes defect coordinates detected by a defect inspection apparatus 10; 62, a low-magnification SEM imaging region; and 63, a defect region that is made larger than the SEM imaging region by an error component (including the error component of the stage 107) possessed by the defect inspection apparatus 10. The design information cut-out section 1161 cuts out the design information about the peripheral region 64 of a defect, which is centered around defect coordinates 61, from the storage section 117, which stores design information. Next, in accordance with the cut-out design information, the defect detection method setup section 1162 searches a portion other than the defect region 63 for a reference region designed to have the same appearance as the defect region 63. In the example shown in FIG. 9, region 65 is a reference region that is designed to have the same appearance as defect region 63. Such a region may be searched by using the geometrical information included in the design information about the peripheral region 64 or by using an image equivalent of the geometrical information. It is assumed that the peripheral region 64 around a defect (defect coordinates 61) is a SEM imaging region that is centered around the defect coordinates 61 to pick up an SEM image without moving the stage 107. This eliminates the necessity of moving the stage 107, on which a sample (semiconductor wafer) 106 is mounted, when picking up an SEM image of a reference image, thereby making it possible to reduce the SEM imaging time.

Next, in step S24, after the defect detection method for each defect is set up, the processing recipe setup section 1163 sets up an execution sequence (operation sequence), which is a combination of (a) a SEM imaging process, (b) a defect detection process, and (c) a defect detection method setup process, and parameters for each process as a loop 2 processing recipe in a manner described later with reference to FIGS. 10A, 10B, and 11, and stores such a processing recipe in the storage section 114.

Then, in loop 2, the overall control section 112 reads processing IDs (a) to (c) and processing parameters (defect ID, image type, coordinates, magnification, defect detection method, reference image index, etc.) of one process from the processing recipe, which is set up in step S24, stored in the storage section 114, and shown in FIG. 11, in accordance with an execution sequence (operation sequence) (step S31), and performs an execution in accordance with the read processing parameters for one processing ID. The processing ID indicates which of three different processes is to be executed. The three different processes are (a) a SEM imaging process in which a local SEM image is picked up at specified coordinates and at a specified magnification, (b) a defect detection process in which a local SEM image of a specified defect is used to detect a defect by a preselected defect detection method, and (c) a defect detection method setup process in which a local SEM image picked up at a high magnification is used to set up a defect detection method in accordance with the position of and the design information about a defect that is detected from a local SEM image picked up at a low magnification. The overall control section 112 performs an execution for a review target defect until the whole process specified by a stored processing recipe is completed, thereby making it possible to automatically collect local SEM images picked up at a high magnification. It is assumed that the storage section 115 stores all the picked-up local SEM images.

In process (a), a local SEM image (defect local SEM image, reference local SEM image, etc.) is picked up at specified coordinates and at a specified magnification (low magnification or high magnification) (step S32). In process (b), a local SEM image of a specified defect is used to detect a defect by a preselected defect detection method (step S33). In process (c), the defect detection method for a local SEM image picked up at a high magnification is set up in accordance with the position of and the design information about a defect that is detected from a local SEM image picked up at a low magnification (step S34). The processing recipe defined in step S24 is set up so as to pick up a high-magnification image of defect coordinates that are detected from a local SEM image picked up at a low magnification, and changed as needed to incorporate a new image pickup procedure.

Figure 12:
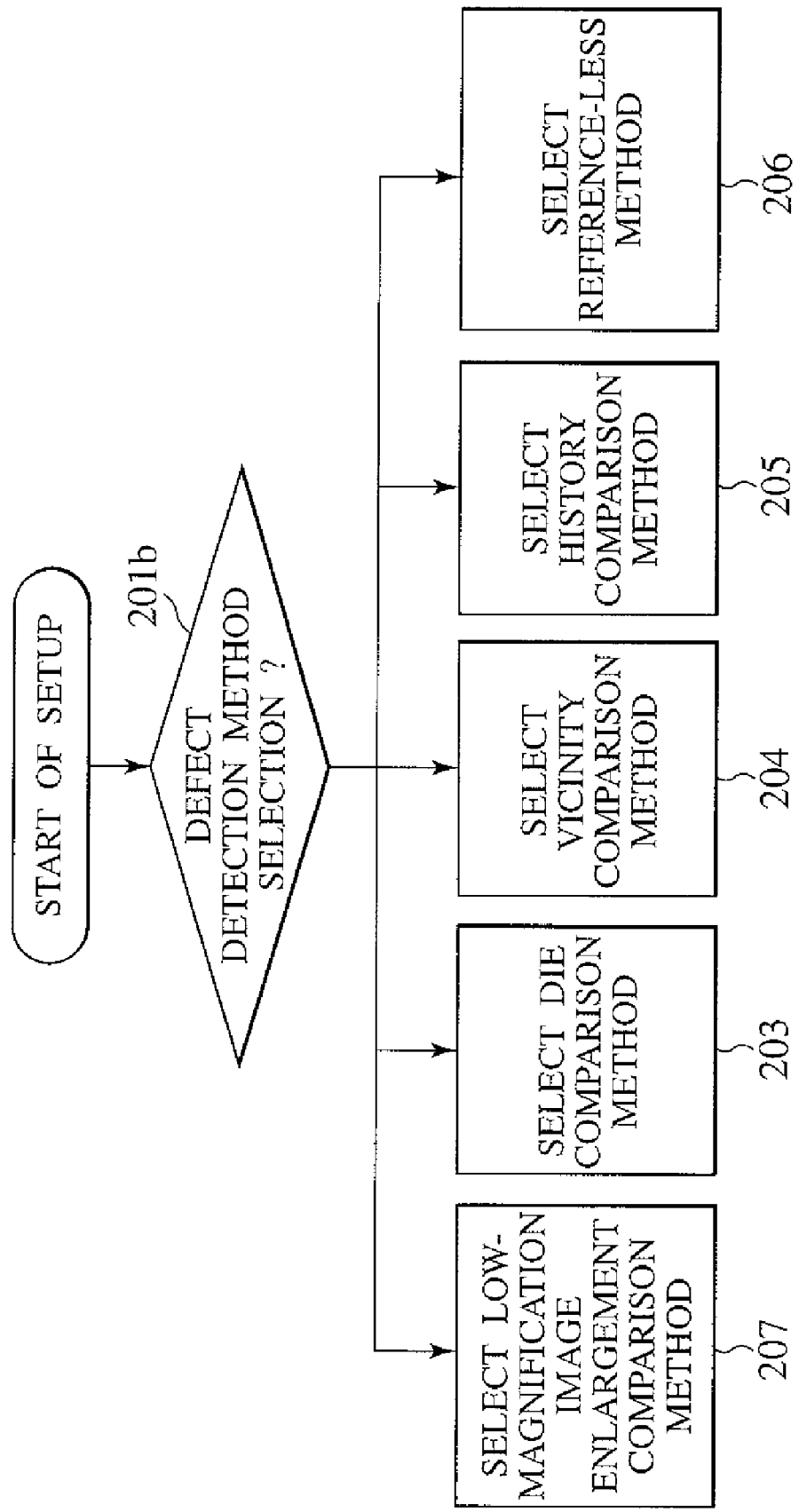
FIG. 12 is a schematic flowchart illustrating an embodiment of defect detection method selection for a high-magnification defect local SEM image.

In step S34, the design information computation section 116 makes a defect detection method selection (201b) for a high-magnification local SEM image that is selected and set up in accordance with the defect coordinates of a sample that are detected from a local SEM image picked up at a low magnification and with the design information about the sample. As shown in FIG. 12, it is conceivable that the design information computation section 116 may select a low-magnification image enlargement comparison method (207) in addition to the aforementioned die comparison method (203), vicinity comparison method (204), history comparison method (205), and reference-less method (206). The low-magnification image enlargement comparison method (207) may be selected to use an enlarged reference local SEM image, which is obtained by performing image processing on a part of a low-magnification reference local SEM image, because the low-magnification reference local SEM image is already acquired in operation sequences 1, 2, and 7.

More specifically, in step S34, the design information cut-out section 1161 and defect detection method setup section 1162 use the design information about a defect region cut out in step S21 and the defect coordinates detected from a defect local SEM image picked up at a low magnification as the input, and set up a defect detection method (201b) by selecting the low-magnification image enlargement comparison method (207), die comparison method (203), vicinity comparison method (204), history comparison method (205), or reference-less method (206).

Figure 13:
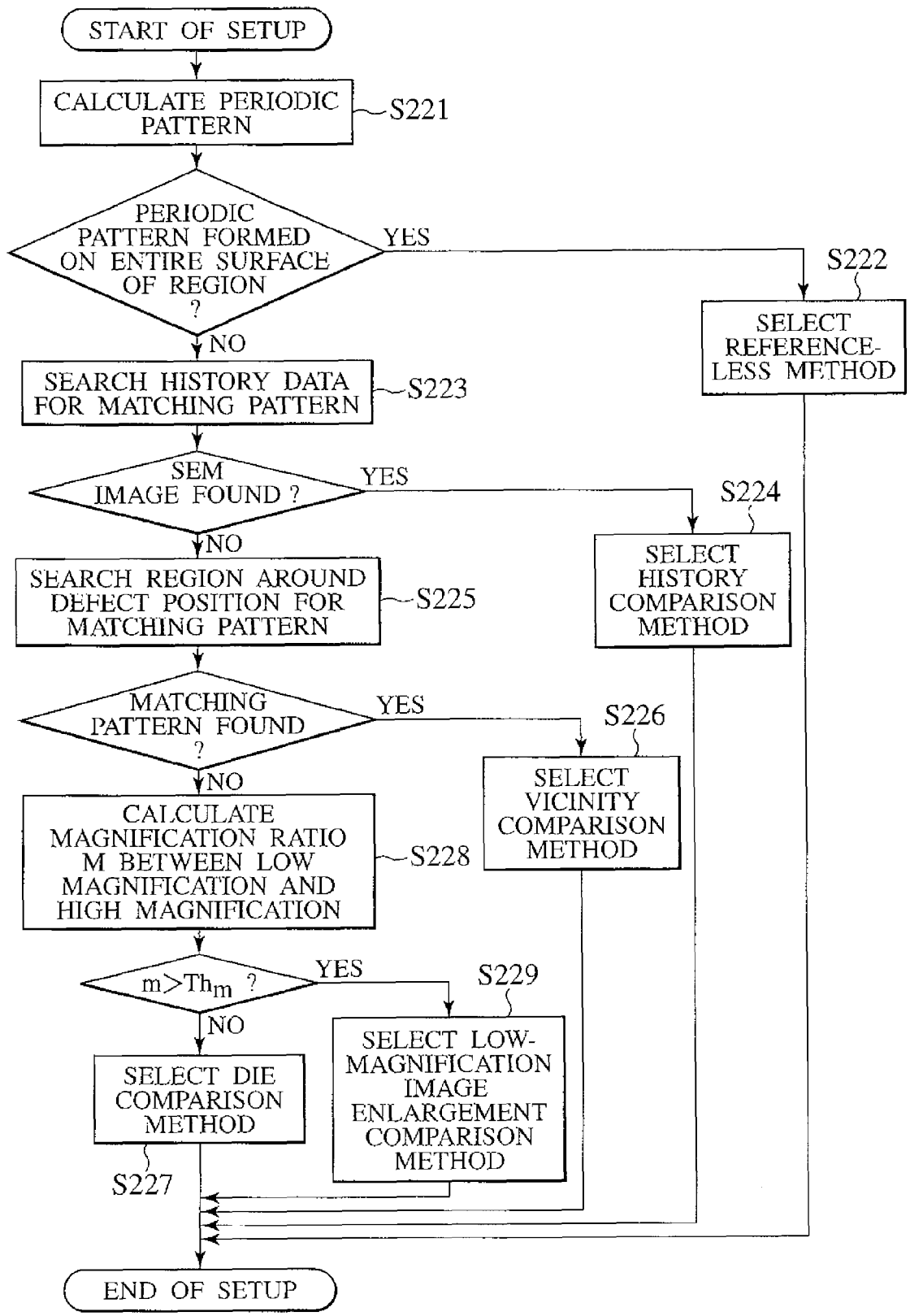
FIG. 13 is a flowchart illustrating the first embodiment of a defect detection method setup process for a high-magnification defect local SEM image.

The defect detection method selection (201b) in step S34 will now be described with reference to FIG. 13. The process performed in steps S221 to S226, which is a part of a defect detection method selection (201b) in step S34, will not be redundantly described because it is the same as the process for setting up a defect detection method from the local SEM image picked up at a low magnification, which is shown in FIG. 6. When a defect is to be detected from a defect local SEM image picked up at a high magnification, the operation for picking up an enlarged reference local SEM image can be omitted by using an SEM image that is enlarged by performing image processing on a part of a reference local SEM image, which is used to detect a defect from a defect local SEM image picked up at a low magnification, as an enlarged reference local SEM image. However, when a great enlargement factor is provided by image processing, the difference between a high-magnification defect local SEM image and an enlarged reference local SEM image becomes significant even in a portion other than a defect region, thereby leading to an erroneous defect detection. Therefore, as shown in FIG. 13, the overall control section 112, for example, calculates the magnification ratio m between a low magnification and a high magnification (step S228). If the magnification ratio m is smaller than a predefined threshold value $Th_m$ ($m<Th_m$), the image processing/classification computation section 113, for example, enlarges a part of a reference local SEM image picked up at a low magnification, which is stored in the storage section 115, and stores the resulting enlarged reference local SEM image in the storage section 115. The defect detection method setup section 1162 then selects the low-magnification image enlargement comparison method (207), which uses the enlarged reference local SEM image stored in the storage section 115 (step S229). If, on the other hand, the magnification ratio m is greater than the threshold value $Th_m$ ($m>Th_m$), the defect detection method setup section 1162 selects the die comparison method (203) (step S227).

A processing recipe setup method that the processing recipe setup section 1163 uses to set up a processing recipe in step S24 will now be described with reference to FIGS. 10A and 10B. FIG. 10A is a diagram illustrating the design information 701 about a die coordinate system of a semiconductor wafer. It collectively indicates the defect coordinates of review target defects (A) to (E) of a sample in accordance with the die coordinates of each defect. It is now presumed that the design information computation section 116 performs steps S21 to S23 to select the vicinity comparison method, which compares defect region 702 against a vicinity reference region 707, for defect (A), select the reference-less method, which relates to defect region 703, for defect (B), select the history comparison method, which compares defect region 704 against a history reference region 707, for defect (C), and select the die comparison method, which compares regions 705 and 706, for defects (D) and (E). FIG. 10B is a diagram illustrating an example of an imaging sequence (operation sequence) (721-727) specified by a processing recipe that is set up by the processing recipe setup section 1163 in accordance with defect detection methods for individual defects and defect coordinates of a sample (wafer coordinates) over which a plurality of dies are two-dimensionally arranged.

When a defect detection method is set up in advance by the defect detection method setup section 1162, the coordinates of the regions (721-727) to be imaged are determined. In the examples shown in FIGS. 10A and 10B, for example, a reference local SEM image for use with the die comparison method concerning defects (D) and (E) needs to be picked up in each of neighboring regions 722, 721 in addition to defect local SEM images (706, 702, 703, 705, 704) that are picked up to contain defects (E), (A), (B), (D), and (C) in imaging regions 723 to 727. In imaging region 724, it is necessary to pick up a low-magnification defect local SEM image (702) and a vicinity's low-magnification reference local SEM image (707).

Figure 10A:
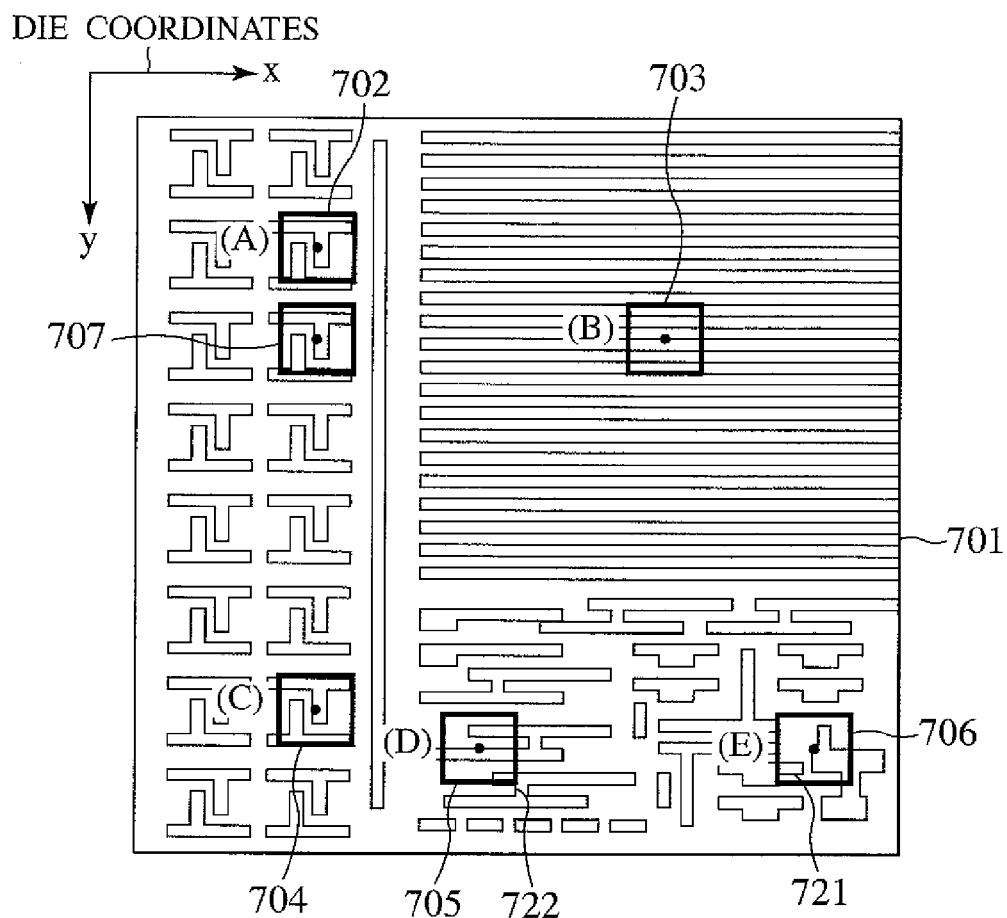
FIG. 10A is a diagram illustrating an example of a collective indication of defect coordinates of defects (A) to (E), which is based on the design information about a die coordinate system of a semiconductor wafer according to the present invention.
Figure 10B:
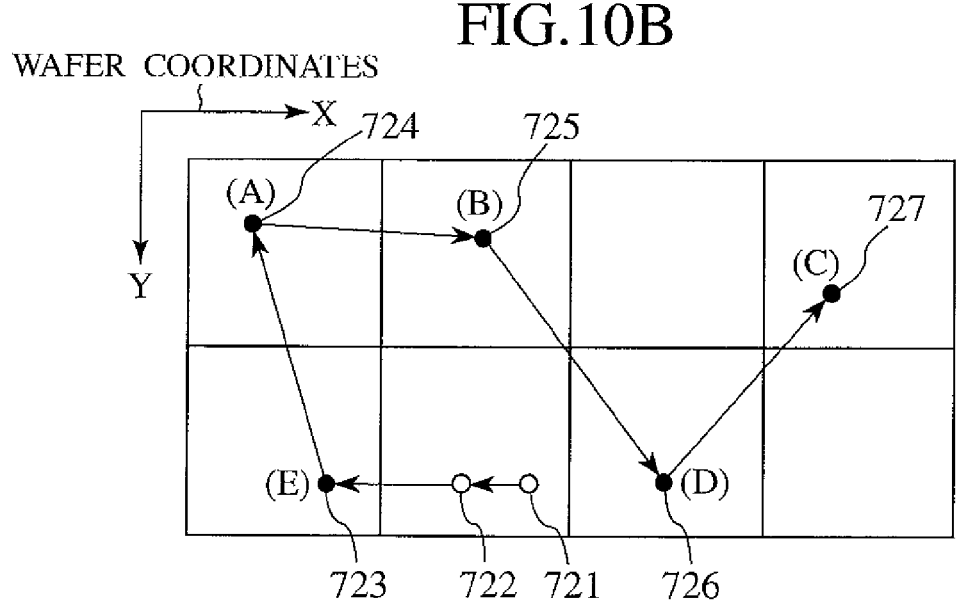
FIG. 10B is a diagram illustrating an example of an imaging sequence (operation sequence) specified by a processing recipe that is set up by a processing recipe setup section in accordance with defect detection methods for individual defects and defect coordinates of a sample (wafer coordinates) over which a plurality of dies are two-dimensionally arranged.

A method of setting up a processing recipe on the basis of the imaging sequence (721-727), which is defined as shown in FIG. 10B, will now be described. A defect detection process can be performed after local SEM images (defect local SEM image and reference local SEM image) necessary for the detection of a defect are picked up. After a defect is detected from a local SEM image picked up at a low magnification, a defect detection method (203-207) can be set up in accordance with the coordinates for imaging at a high magnification on the basis of the coordinates of the detected defect and with a local SEM image picked up at the high magnification.

As described above, the processing recipe setup section 1163 sets up the imaging sequence, the execution sequence (operation sequence), which is a combination of the defect detection process and defect detection method setup process, and the parameters (defect ID, image type, coordinates, magnification, defect detection method, reference image index, etc.) for each process as a processing recipe and stores it in the storage section 114 (FIG. 11). More specifically, in operation sequence (execution sequence) 1, a reference local SEM image (reference image index 1) (721) of defect (E) (x1,y1) for die comparison is picked up at a low magnification as processing ID (a). Next, in operation sequence (execution sequence) 2, a reference local SEM image (reference image index 2) (722) of defect (D) (x2,y2) for die comparison is picked up at a low magnification as processing ID (a). Next, in operation sequence 3, a defect local SEM image (706) of defect (E) (x3,y3) in imaging region 723 is picked up at a low magnification as processing ID (a). Next, in operation sequence 4, the position coordinates of defect (E) at a low magnification are calculated by making a die comparison between a low-magnification defect local SEM image (706) of defect (E) and a low-magnification reference local SEM image (721) of defect (E). Next, in operation sequence 5, a defect detection method (e.g., low-magnification image enlargement comparison method) that uses a high-magnification local SEM image is selected in accordance with the design information about defect region 706, which is cut out from the design information about defect (E), and with the calculated position coordinates of defect (E) at a low magnification. Next, in operation sequence 6, a high-magnification defect local SEM image is picked up as processing ID (a) in accordance with the calculated position coordinates (x4,y4) of defect (E) at a low magnification. Next, in operation sequence 7, a reference local SEM image (reference image index 3) (707) of defect (A) (x5,y5) for making a vicinity comparison in imaging region 724 is picked up at a low magnification as processing ID (a). Next, in operation sequence 8, a defect local SEM image (702) of defect (A) in imaging region 724 is picked up at a low magnification as processing ID (a). Next, in operation sequence 9, the position coordinates of defect (A) at a low magnification are calculated by making a vicinity comparison between a low-magnification defect local SEM image (702) of defect (A) and a low-magnification reference local SEM image (707) of defect (A). . . . Next, in operation sequence 18, the position coordinates of defect (C) at a low magnification are calculated by making a history comparison between a low-magnification defect local SEM image (704) of defect (C) and a low-magnification history reference local SEM image (707) of defect (C). Next, in operation sequence 19, a defect detection method (e.g., low-magnification image enlargement comparison method) that uses a high-magnification local SEM image is selected in accordance with the design information about defect region 704, which is cut out from the design information about defect (C), and with the calculated position coordinates of defect (C) at a low magnification. Next, in operation sequence 20, a high-magnification defect local SEM image is picked up as processing ID (a) in accordance with the calculated position coordinates (x13,y13) of defect (C) at a low magnification.

Figure 14:
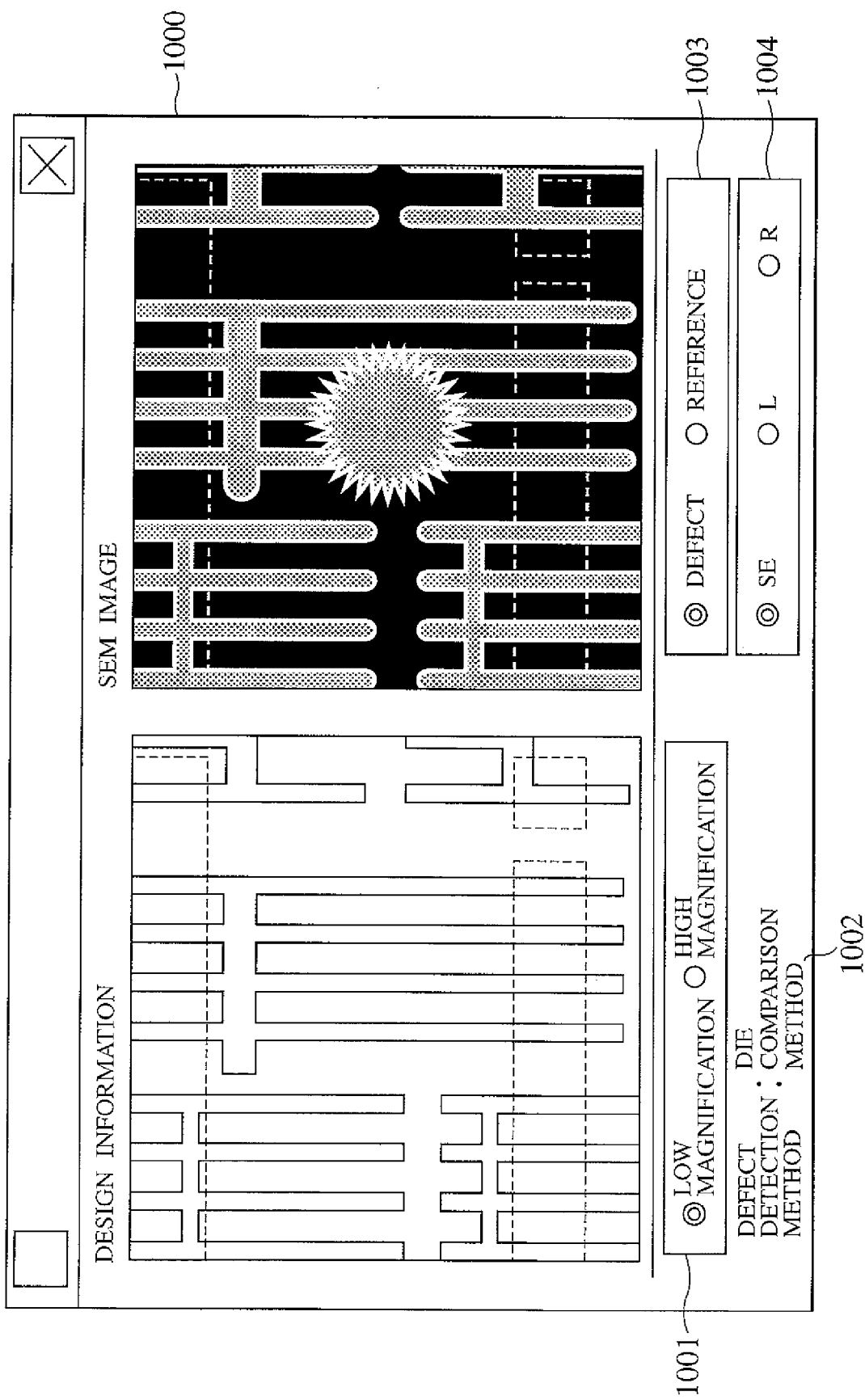
FIG. 14 illustrates an embodiment of an interface (GUI).

An example of an interface (GUI) provided in the defect review apparatus (review SEM) according to the present invention will now be described with reference to FIG. 14. The interface 1000 displays a picked-up SEM image and the design information (design data) about a region that correlates with the imaging region of the SEM image, and includes a button 1001 for switching the picked-up SEM image and cut-out design information between low magnification and high magnification, an area 1002 for displaying a selected defect detection method, a button 1003 for switching between a defect SEM image and a reference SEM image (including a synthesized reference image), and a button 1004 for selecting the SE (Secondary Electron), L (Left), or R (Right) mode for the picked-up SEM image. It should be noted that the interface 1000 may display the design information (design data) and SEM image in an overlay mode.

It is assumed that the embodiment described above uses a scanning electron microscope. However, an apparatus other than a scanning electron microscope may be used as the means of image acquisition. Further, the embodiment described above has been described on the assumption that a semiconductor wafer is used as a sample. However, the present invention is not limited to the review of a semiconductor wafer. For example, the present invention is also applicable to a situation where defects of a liquid crystal panel, plasma display panel, magnetic head, magnetic disk, or other sample are to be reviewed.

Second Embodiment

Figure 15:
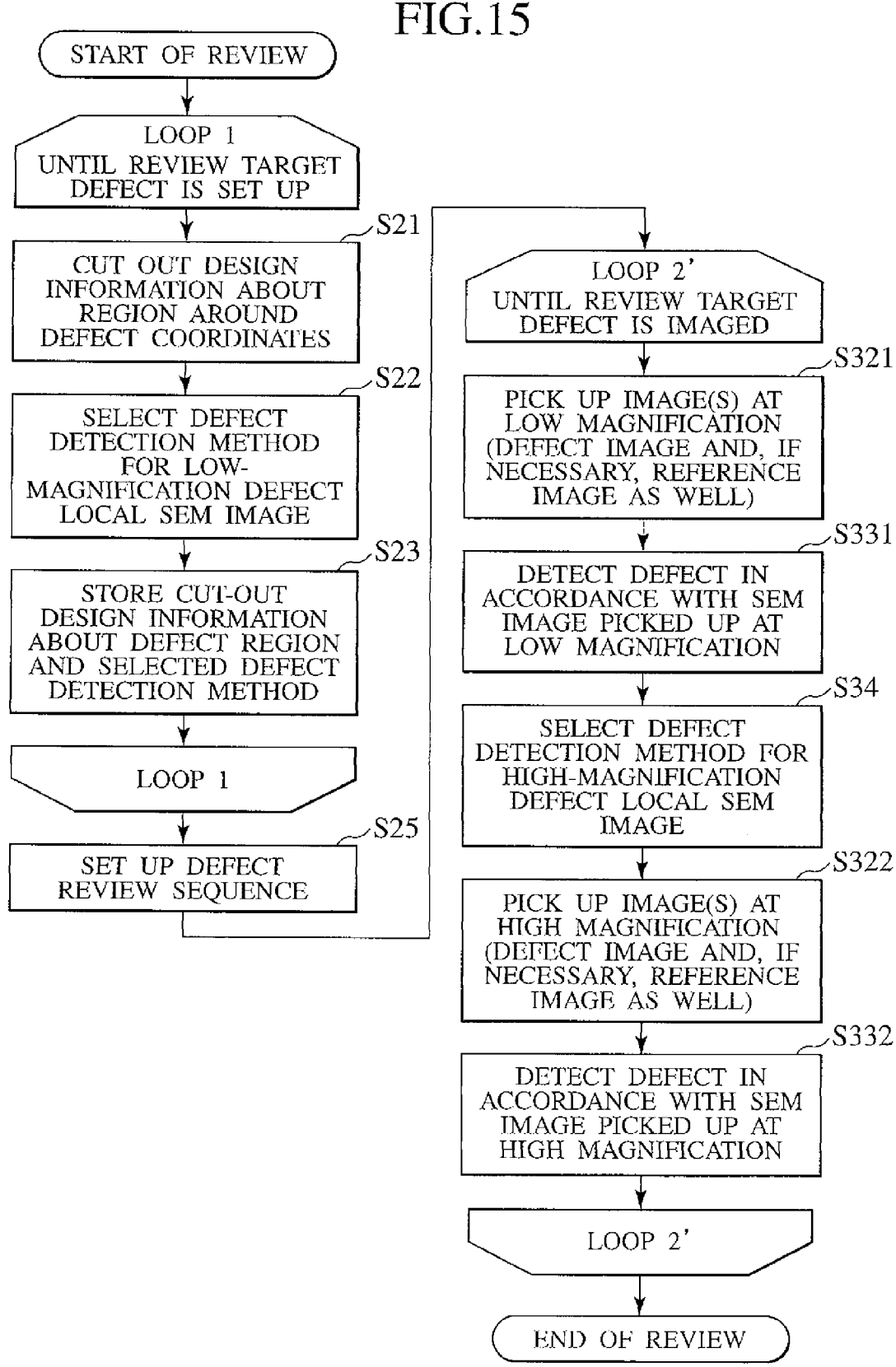
FIG. 15 is a flowchart illustrating a second embodiment of an ADR sequence that is performed by a review-SEM-based defect review apparatus.

A review SEM (Scanning Electron Microscope) that is a second embodiment of the present invention of a method and apparatus for reviewing defects will now be described. The second embodiment has the same hardware configuration and interface as the first embodiment, and automatically picks up and collects defect SEM images in a sequence indicated in FIG. 15.

As shown in FIG. 3, the first embodiment performs steps S21 to S23 to select a defect detection method in advance for a review target defect, which is detected by a defect detection apparatus, and performs step S24 to set up a processing recipe in accordance with the selected defect detection method and detected defect coordinates. The second embodiment, on the other hand, performs steps S21 to S23 to select a defect detection method in advance for a review target defect, which is detected by the defect detection apparatus 10, and performs step S25 to define a defect review sequence in accordance with the detected defect coordinates. In the second embodiment, a loop 2' process (steps S321, S331, S34, S322, and S332) is performed on a review target defect to pick up a defect image (including, if necessary, a reference image) and detect defect coordinates.

Before the SEM image acquisition section 121 picks up an image, the design information computation section 116 performs a loop 1 process (steps S21 to S23) to select a defect detection method for a low-magnification defect local SEM image of a review target defect. First of all, the design information computation section 116 cuts out the design information about a defect region around the coordinates of a defect (step S21), selects a defect detection method (203-206) for a defect local SEM image that is to be picked up at a low magnification in accordance with the cut-out design information about the defect region (step S22), stores the cut-out design information about the defect region in the storage section 115, and stores the relationship between the selected defect detection method and a defect ID in the storage section 114 (step S23).

Next, as shown in FIG. 10B, the design information computation section 116 defines a review sequence (721-727) for defects (A) to (E), including the review of a reference image, as shown in FIG. 10B, and stores the review sequence in the storage section 114 in accordance with the defect coordinates (including die coordinates) of a sample, which are collectively shown within a die as indicated in FIG. 10A, and with the design information 701, for instance, about the interior of the die (step S25). The review sequence for the defects is defined so as to minimize the distance of stage movement between the defects.

When a review is to be conducted, the SEM image acquisition section 121 performs steps S321, S331, S34, S322, and S332 under the control of the overall control section 112 to pick up an SEM image of the defects in the defined review sequence. First of all, step S321 is performed to pick up a defect SEM image at a low magnification and, if necessary, pick up a reference SEM image as well. The necessity of picking up a reference SEM image depends on the defect detection method selected in step S22 (when, for instance, the die comparison method is selected, it is necessary to pick up a reference SEM image from a neighboring die). Next, the image processing/classification computation section (defect detection section) 113 detects a defect in accordance a defect SEM image, which is picked up at a low magnification by the defect detection method selected in step S22 (step S331). The design information computation section 116 then performs step S34 to set up a defect detection method for a high-magnification defect local SEM image in accordance with the design information cut out in step S21 and the defect coordinates detected in step S331. Subsequently, step S332 is performed to pick up a defect SEM image at a high magnification and, if necessary, a reference SEM image as well. Finally, the image processing/classification computation section (review process section) 113 performs step S332 to accurately detect the position coordinates of a defect in accordance with a defect SEM image that is picked up at a high magnification by the defect detection method selected in step S34.

The setup process in step S25 may be performed in parallel with the process in steps S21 to S23.

Third Embodiment

Figure 16:
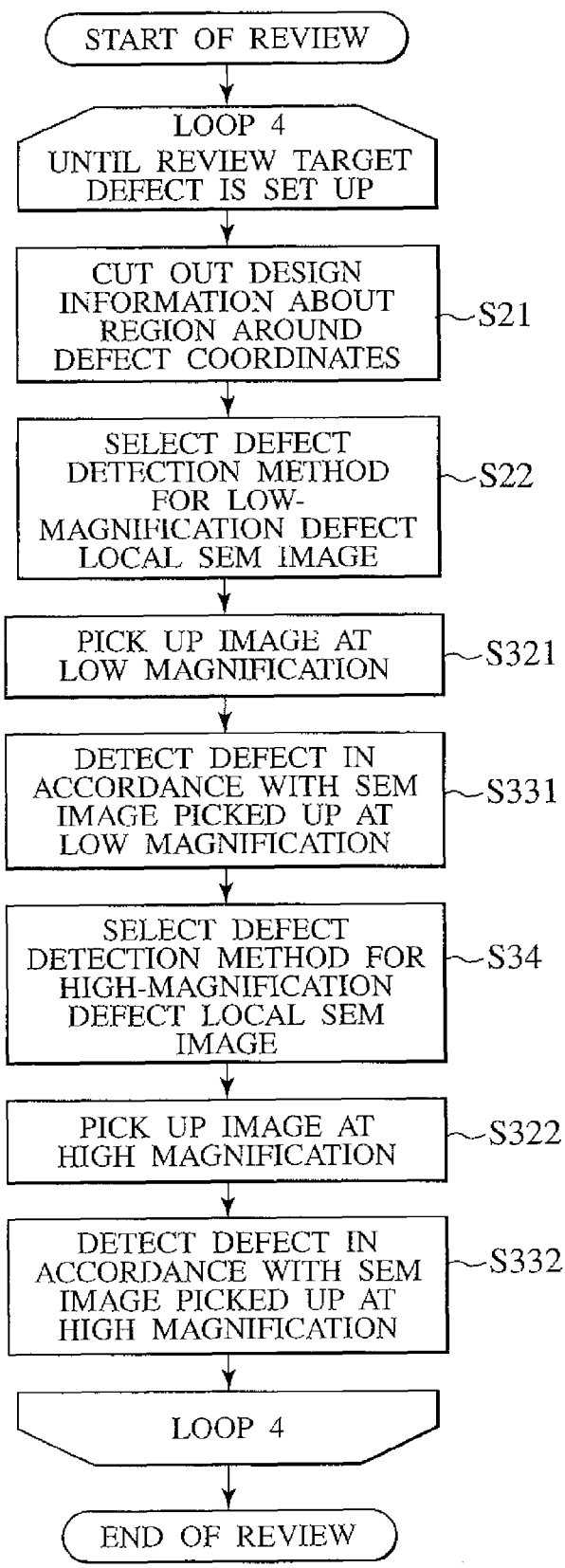
FIG. 16 is a flowchart illustrating a third embodiment of an ADR sequence that is performed by a review-SEM-based defect review apparatus.

A review SEM (Scanning Electron Microscope) that is a third embodiment of the present invention of a method and apparatus for reviewing defects will now be described. The third embodiment has the same hardware configuration and interface as the first embodiment, and automatically picks up and collects defect SEM images in a sequence indicated in FIG. 16.

The first embodiment sets up a defect detection method in advance for all review target defects and then picks up a local SEM image. On the other hand, the third embodiment sets up a defect detection method for each defect image pickup in a sequence shown in FIG. 16. More specifically, the third embodiment picks up a defect SEM image and detects a defect by performing steps S21, S22, S321, S331, S34, S322, and S332 for all review target defects. First of all, the design information computation section 116 cuts out the design information about a defect region in step S21, and selects a defect detection method for a low-magnification defect local SEM image in accordance with the cut-out design information about a defect region by using the method described in connection with the first embodiment (step S22). Next, the SEM image acquisition section 121 picks up an SEM image at a low magnification under the control of the overall control section 112 (step S321). If a reference local SEM image for conducting a comparative inspection by the defect detection method selected in step S22 is needed, it is picked up in step S321. Next, the image processing/classification computation section 113 detects a defect by using the defect detection method selected in step S22 in accordance with an SEM image picked up at a low magnification. The design information computation section 116 then sets up a defect detection method for a high-magnification defect local SEM image in accordance with the design information about a defect region, which is cut out in step S21, and defect coordinates detected in step S331 by using the method described in connection with the first embodiment (step S34). Next, the SEM image acquisition section 121 picks up an SEM image at a high magnification under the control of the overall control section 112 (step S322). If a reference local SEM image for conducting a comparative inspection by using the defect detection method selected in step S34 is needed, it is picked up in step S322. Next, the image processing/classification computation section 113 detects a defect (step S332) in accordance with an SEM image, which is picked up at a high magnification, by using the defect detection method selected in step S34.

Steps S34 and S322 may be performed in parallel. Further, SEM image pickup steps S321 and S322 may be performed in parallel with defect detection method setup steps S21 and S22 for the next defect.

The present invention may be embodied in other specific forms without departing from the spirit or essential characteristics thereof. The present embodiments are therefore to be considered in all respects as illustrative and not restrictive, the scope of the present invention being indicated by the appended claims rather than by the foregoing description, and all changes which come within the meaning and range of equivalency of the claims are therefore intended to be embraced therein.

What is claimed is:

1. A method for reviewing a defect, comprising the steps of:
   design information cutting out step for cutting out a design information of a defect region on a sample including coordinate information of a defect detected with an inspection apparatus by using defect information of the sample detected beforehand by the inspection apparatus and design information of the sample;
   defect detection method selecting step for selecting defect detection method according to repetitiveness of patterns formed on the sample which is calculated from the design information of the defect region cut out by the design information cutting out step;
   first image acquisition step for acquiring an image of the defect on the sample with a first amplification, which is detected beforehand by the inspection apparatus, under a first defect detection method selected from plural defect detection methods by the defect detection method selecting step;
   defect detection step for detecting the defect from the image obtained by the first image acquisition step under the first defect detection method selected by the defect detection method selecting step; and
   second imaging step for imaging the defect detected by the defect detection step with a second amplification.

2. The method according to claim 1, wherein defect detection selecting step includes at least one of a reference-less method, a die comparison method, a vicinity comparison method, a history comparison method and a combination thereof.

3. The method for reviewing defects according to claim 1, wherein in the defect detection method selecting step, the defect detection method is selected by an existence of repetitiveness of the patterns formed on the sample which is judged from the design information of the defect region cut out by the design information cutting out step.

4. The method for reviewing defects according to claim 1, wherein in the defect detection method selecting step, the defect detection method is selected by a similarity of a circuit pattern included in the design information cut out by the design information cutting out step with a peripheral circuit pattern of the cut out circuit pattern.

5. The method for reviewing defects according to claim 1, wherein in the design information cutting out step, a history data of the design information is cut out, and wherein in the defect detection method selecting step, the defect detection method is selected by the cut out history data of the design information.

6. The method for reviewing defects according to claim 1, wherein in the design information cutting out step, a history data of the design information is cut out, and wherein in the defect detection method selecting step, the defect detection method is selected by information of a circuit pattern included in the design information cut out by the design information cutting out step and the cut out history data.

7. The method for reviewing defects according to claim 1, wherein in the design information cutting out step, a history data of the design information is cut out, and wherein in the defect detection method selecting step includes at least one of judging existence of repetitiveness of the patterns formed on the sample from the design information of the defect region cut out by the design information cutting out step, judging existence of a pattern in a peripheral region around the defect which is identical to a pattern included in the design information cut out by the design information cutting out step and judging identity of the circuit pattern included in the cut out design information with any one of plural design information cut out from the history data.

8. The method for reviewing defects according to claim 1, wherein in the design information cutting out step, in a case the die comparison method or the vicinity comparison method is selected, the first imaging step includes acquiring a reference image.

9. An apparatus for reviewing a defect, comprising:
design information cutting out unit which cuts out a design information of a defect region on a sample including coordinate information of a defect detected with an inspection apparatus by using defect information of the sample detected beforehand by the inspection apparatus and design information of the sample;
defect detection method selecting unit which selects defect detection method according to repetitiveness of patterns formed on the sample which is calculated from the design information of the defect region cut out by the design information cutting out unit;
first image acquisition unit which acquires an image of the defect on the sample with a first amplification, which is detected beforehand by the inspection apparatus, under a first defect detection method selected from plural defect detection methods by the defect detection method selecting unit;
defect detection unit which detects the defect from the image obtained by the first image acquisition unit under the first defect detection method selected by the defect detection method selecting unit; and
second imaging unit which images the defect detected by the defect detection unit with a second amplification.

10. The apparatus for reviewing a defect according to claim 9, wherein defect detection methods to be selected by the defect detection method selecting unit includes at least one of a reference-less method, a die comparison method, a vicinity comparison method, a history comparison method and a combination thereof.

11. The apparatus for reviewing a defect according to claim 9, wherein in the defect detection method selecting unit, the defect detection method is selected by an existence of repetitiveness of the patterns formed on the sample which is judged from the design information of the defect region cut out by the design information cutting out unit.

12. The apparatus for reviewing defects according to claim 9, wherein in the defect detection method selecting unit, the defect detection method is selected by a similarity of a circuit pattern included in the design information cut out by the design information cutting out unit with a peripheral circuit pattern of the cut out circuit pattern.

13. The apparatus for reviewing defects according to claim 9, wherein the design information cutting out unit cut out a history data of the design information, and wherein the defect detection method selecting unit selects the defect detection method by the cut out history data of the design information.

14. The apparatus for reviewing defects according to claim 9, wherein the design information cutting out unit cut out a history data of the design information, and wherein the defect detection method selecting unit selects the defect detection method by using information of a circuit pattern included in the design information cut out by the design information cutting out unit and the cut out history data.

15. The apparatus for reviewing defects according to claim 9, wherein the design information cutting out unit cut out a history data of the design information, and wherein the defect detection method selecting unit judges at least one of existence of repetitiveness of the patterns formed on the sample from the design information of the defect region cut out by the design information cutting out unit, existence of a pattern in a peripheral region around the defect which is identical to a pattern included in the design information cut out by the design information cutting out unit and identity of the circuit pattern included in the cut out design information with any one of plural design information cut out from the history data.

16. The apparatus for reviewing defects according to claim 9, wherein in a case the design information cutting out unit selects the die comparison method or the vicinity comparison method, the first imaging unit acquires a reference image.

* * * * *